US012532916B2

(12) United States Patent
Phillips et al.

(10) Patent No.: US 12,532,916 B2
(45) Date of Patent: Jan. 27, 2026

(54) THIN PLATE HEATING ELEMENTS FOR MICRO-VAPORIZERS

(71) Applicant: Blackship Technologies Development LLC, North Chesterfield, VA (US)

(72) Inventors: Donovan Phillips, North Chesterfield, VA (US); Yongjie Xu, North Chesterfield, VA (US)

(73) Assignee: Blackship Technologies Development LLC, North Chesterfield, VA (US)

( * ) Notice: Subject to any disclaimer, the term of this patent is extended or adjusted under 35 U.S.C. 154(b) by 770 days.

(21) Appl. No.: 17/117,373

(22) Filed: Dec. 10, 2020

(65) Prior Publication Data

US 2022/0183361 A1 Jun. 16, 2022

(51) Int. Cl.

| | |
|---|---|
| ***A24F 40/46*** | (2020.01) |
| ***A24F 40/10*** | (2020.01) |
| ***A24F 40/44*** | (2020.01) |
| ***A24F 40/48*** | (2020.01) |
| ***H05B 3/03*** | (2006.01) |
| ***H05B 3/12*** | (2006.01) |

(Continued)

(52) U.S. Cl.

CPC .............. *A24F 40/46* (2020.01); *A24F 40/10* (2020.01); *A24F 40/44* (2020.01); *A24F 40/48* (2020.01); *H05B 3/03* (2013.01); *H05B 3/12* (2013.01); *H05B 3/24* (2013.01); *A61M 15/06* (2013.01); *H05B 2203/008* (2013.01); *H05B 2203/016* (2013.01)

(58) Field of Classification Search

CPC ........................................................ A24F 40/46

See application file for complete search history.

(56) References Cited

U.S. PATENT DOCUMENTS

| | | | |
|---|---|---|---|
| 5,878,752 | A | 3/1999 | Adams et al. |
| 9,055,617 | B2 | 6/2015 | Thorens et al. |
| 10,172,388 | B2 | 1/2019 | Sears et al. |

(Continued)

FOREIGN PATENT DOCUMENTS

| | | | |
|---|---|---|---|
| WO | 2020132079 | A1 | 6/2020 |
| WO | 2020223876 | A1 | 11/2020 |

OTHER PUBLICATIONS

International Searching Authority, International Search Report and Written Opinion, International Application No. PCT/US21/62528, Feb. 23, 2022, pp. 1-17.

*Primary Examiner* — Michael J Felton
*Assistant Examiner* — Courtney G Culbert
(74) *Attorney, Agent, or Firm* — Nixon & Vanderhye P.C.

(57) ABSTRACT

A vaporizer heating element has a heating element body formed from a single sheet of electrically conductive material having a constant sheet thickness. A peripheral conduction portion has spaced apart positive and negative support arms each having an interior edge. A central heating portion has a plurality of parallel heating strips, spaces between the heating strips defining flow channels through the element body. The central heating portion is intermediate the interior edges of the support arms. A first bridge strip connects the interior edge of the positive support arm to the central heating portion and a second bridge strip connects the interior edge of the negative support arm to the central heating portion. A plurality of peripheral support tabs extend from exterior edges of the support arms and a plurality of central support tabs extend from the central heating portion.

37 Claims, 9 Drawing Sheets

(51) Int. Cl.
*H05B 3/24* (2006.01)
*A61M 15/06* (2006.01)

(56) References Cited

U.S. PATENT DOCUMENTS

| | | | | |
|---|---|---|---|---|
| 10,517,331 | B2 | 12/2019 | Atkins et al. | |
| 2009/0126705 | A1 | 5/2009 | Trapasso et al. | |
| 2011/0155153 | A1 | 6/2011 | Thorens et al. | |
| 2016/0309785 | A1 | 10/2016 | Holtz | |
| 2018/0263290 | A1 | 9/2018 | Collett et al. | |
| 2019/0104764 | A1 | 4/2019 | Tucker et al. | |
| 2020/0107585 | A1 | 4/2020 | Atkins et al. | |
| 2020/0114094 | A1 | 4/2020 | Atkins et al. | |
| 2022/0408815 | A1* | 12/2022 | Chen | A24F 40/485 |

* cited by examiner

THIN PLATE HEATING ELEMENTS FOR MICRO-VAPORIZERS

BACKGROUND OF THE INVENTION

The present invention relates generally to micro-vaporizer heaters and, more particularly, to a micro-vaporizer heating element formed from a single thin sheet of conductive material.

Micro-vaporizers are devices in which a vaporizable liquid is drawn from a storage reservoir into a chamber where it is heated to vaporization temperature by a heating element. The vaporized liquid is then drawn or forced from the chamber. In products such as electronic cigarettes (also known as e-cigarettes or personal vaporizers), the vaporized liquid is drawn from the chamber through a mouthpiece and inhaled by the user. In other products the vaporized liquid is dispersed into the atmosphere.

Conventional micro-vaporizer heaters typically include a coiled heating wire in close proximity to or wrapped around a wick that draws the vaporizable liquid from the reservoir. Coiled wire heaters have a number of drawbacks relating to efficiency and cost to manufacture. With the growing popularity of low cost, throwaway personal vaporization devices, a high efficiency, lower cost alternative to such heaters is needed.

SUMMARY OF THE INVENTION

An illustrative aspect of the invention provides a vaporizer heating element comprising a heating element body formed from a single sheet of electrically conductive material having a constant sheet thickness. The heating element body has a peripheral conduction portion comprising spaced apart positive and negative support arms. The support arms each have an interior edge parallel to the interior edge of the other support arm and an exterior edge. The heating element body also has a central heating portion comprising a plurality of spaced apart parallel heating strips. Spaces between the heating strips define first flow channels through the element body. The central heating portion is intermediate, but spaced apart from, the interior edges of the positive and negative support arms. The heating element body also has first and second bridge strips. The first bridge strip connects the interior edge of the positive support arm to the central heating portion and the second bridge strip connects the interior edge of the negative support arm to the central heating portion. A plurality of peripheral support tabs extend from the exterior edge of each of the positive and negative support arms and a plurality of central support tabs extend from the central heating portion.

Another illustrative aspect of the invention provides a vaporizer heating element comprising an electrically conductive element body. The element body has a planar peripheral conduction portion comprising spaced apart positive and negative support arms. Each support arm has an interior edge and an exterior edge. All of the interior and exterior edges of the support arms are parallel to a longitudinal body axis. A plurality of peripheral support tabs extend from the exterior edge of each of the positive and negative support arms. The element body also has a planar central heating portion comprising an array of spaced apart closed loops. Each loop has a pair of parallel edge strips connected to one another at first and second loop ends. The parallel edge strips of the closed loops are all parallel to the longitudinal body axis, and each pair of adjacent loops is connected to one another by a lateral strip. The element body also has a plurality of central support tabs. Each central support tab extends from one of the first and second loop ends of one of the closed loops. A first element connector connects the interior edge of the positive support arm to the central heating portion, and a second element connector connects the interior edge of the negative support arm to the central heating portion.

Another illustrative aspect of the invention provides a vaporizer comprising a housing, a vaporization chamber disposed within the housing in fluid communication with an air inlet and a vaporization product outlet, a reservoir disposed within the housing and configured for selectively retaining a vaporizable liquid, and a liquid transport structure. The liquid transport structure has an intake surface configured for contacting vaporizable liquid in the reservoir and drawing it from the reservoir to an exit surface of the liquid transport structure. The vaporizer also comprises a mono-material, thin plate heating element positioned to form a portion of a first wall of the vaporization chamber. The thin plate heating element has a first side adjacent or in contact with the exit surface of the liquid transport structure and an opposite second side facing an interior space of the vaporization chamber. The thin plate heating element comprises a planar peripheral conduction portion comprising spaced apart positive and negative support arms, and a planar central heating portion in electrical communication with the positive and negative support arms. The central heating portion comprises a plurality of spaced apart parallel heating strips. Spaces between the heating strips define flow channels through the heating element. The thin plate heating element also comprises a plurality of peripheral support tabs extending from an edge of each of the positive and negative support arms. The peripheral support tabs each have a free end in contact with one of the set consisting of a surface of a second wall of the vaporization chamber and the exit surface of the liquid transport structure.

BRIEF DESCRIPTION OF THE DRAWINGS

The invention can be more fully understood by reading the following detailed description together with the accompanying drawing, in which like reference indicators are used to designate like elements, and in which.

DETAILED DESCRIPTION OF THE INVENTION

The present invention provides thin plate heating elements for use in personal vaporizer devices. The heating elements of the invention provide a simple, low cost alternative to prior art heating elements that can be incorporated into throwaway devices and modular cartridges.

Typical micro-vaporizers have a reservoir from which vaporizable liquid is drawn (typically through the use of a wick) to a vaporization chamber. There the liquid is brought into close proximity with a heating element. The heating element and, generally, a portion of the wick are disposed within the vaporization chamber. When the heating element is activated, the liquid from the wick is vaporized/aerosolized. The resulting vaporization products and unvaporized liquid are mixed with air that is drawn from outside the device into the vaporization chamber. The mixture is then released from or drawn out of the device.

Figure 1:
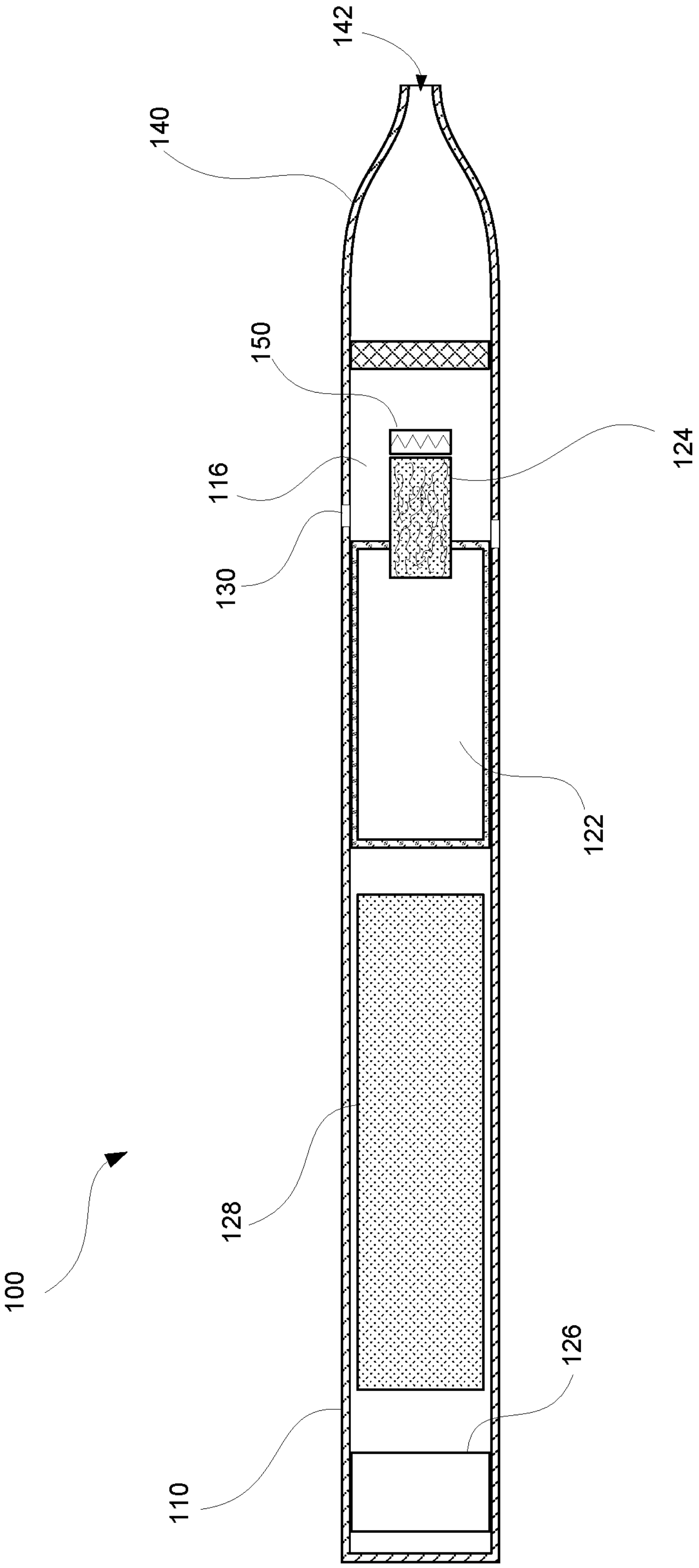
FIG. 1 (Prior Art)
FIG. 1 is a section view of a prior art personal vaporizer.

As shown in FIG. 1, a typical prior art personal vaporizer 100 has an outer case 110 with an air intake passage (or passages) 130 that provide air to a vaporization chamber 116. The personal vaporizer 100 has a liquid reservoir 122 in which is disposed a vaporizable liquid. A liquid transport structure 124 (e.g., a wick) is configured and positioned to be in contact with the liquid in the reservoir 122 and for drawing the liquid out of the reservoir 122 and into the vaporization chamber 116 in close proximity or in contact with a heating element 150. The illustrative personal vaporizer 100 also comprises a battery 128 for powering the heating element 150 and a control unit 126. When the heater 150 is activated, liquid from the liquid transport structure is heated and vaporized and mixed with air in the vaporization chamber 116. The resulting mixture is drawn through into and through a mouthpiece 140 and out through the exit 142 where it is inhaled by the user.

The heating element 150 may be configured to heat the vaporizable liquid through any conductive, convective, and/or radiative heat transfer mechanism. In typical vaporizers, the heating element 150 is or includes a resistance element in the form of a wire coil. As previously noted, coiled wire heating elements have significant drawbacks. While plate-like heating elements have been used in vaporizer devices, they have suffered from many of the same drawbacks as coiled wire heaters. This is due, at least in part, to the requirement for an expensive base material and/or multiple materials and substrates. These aspects may make the resulting heater as expensive as or more expensive than a comparable coiled wire heater. The prior art heaters may also be difficult or impossible to use in conjunction with certain vaporizer housing materials due to heat conduction issues.

The thin plate heating elements of the present invention are manufactured from a single thin sheet of conductive material. The heating elements are formed by cutting a pattern of channels through the material to provide a flow path for vaporizable liquid and vaporization products to flow through. The remaining conductive material defining these channels is formed into an array of thin strips that collectively form a central heating grid. This grid is connected to supporting arms on opposite sides of the grid. While electrically connected to the supporting arms by a pair of bridge elements, the heating grid is largely thermally isolated from the supporting arms. This has the effect of reducing the heat transmitted to the structure supporting the heating element.

Thermal transmission may be further reduced by the use of stand-off tabs that may be included when the heating element is cut from the conductive material sheet. These tabs may be used to attach the heating element to the surrounding vaporizer structure or may simply be used to space the main body of the heating element from certain structural features. While initially coplanar with the central heating grid and the supporting arms, the stand-off tabs may be bent to provide supporting "legs" for the heating element. This allows the heating element to be supported by, but spaced apart from, a particular surface. Alternatively, the stand-off tabs may be used to support another structure while maintaining spacing of that structure from the main body of the heating element. In some embodiments, some tabs may extend in one direction to support the heating element, while other tabs may extend in the opposite direction to support another structure. As will be discussed in more detail hereafter, stand-off tabs may extend from the supporting arms, the central heating grid, or both.

Figure 2:
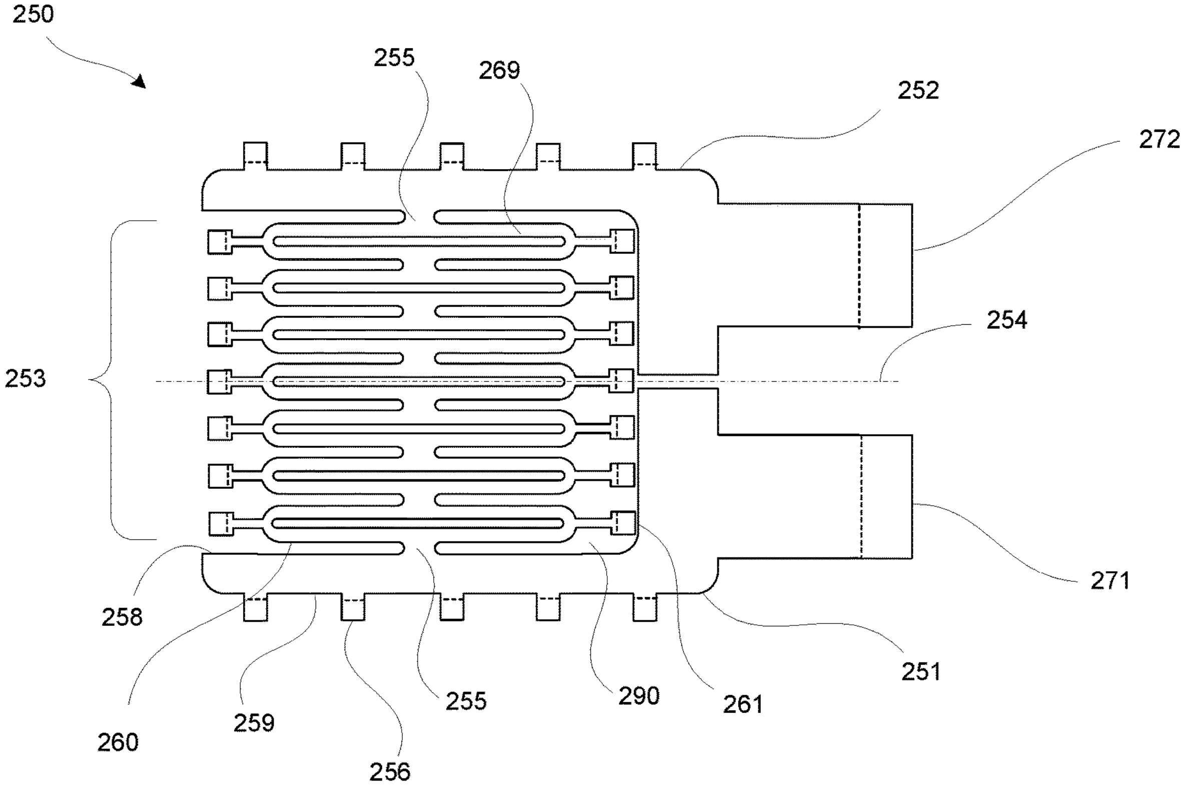
FIG. 2 is a plan view of a thin plate heating element according to an embodiment of the invention.
Figure 3:
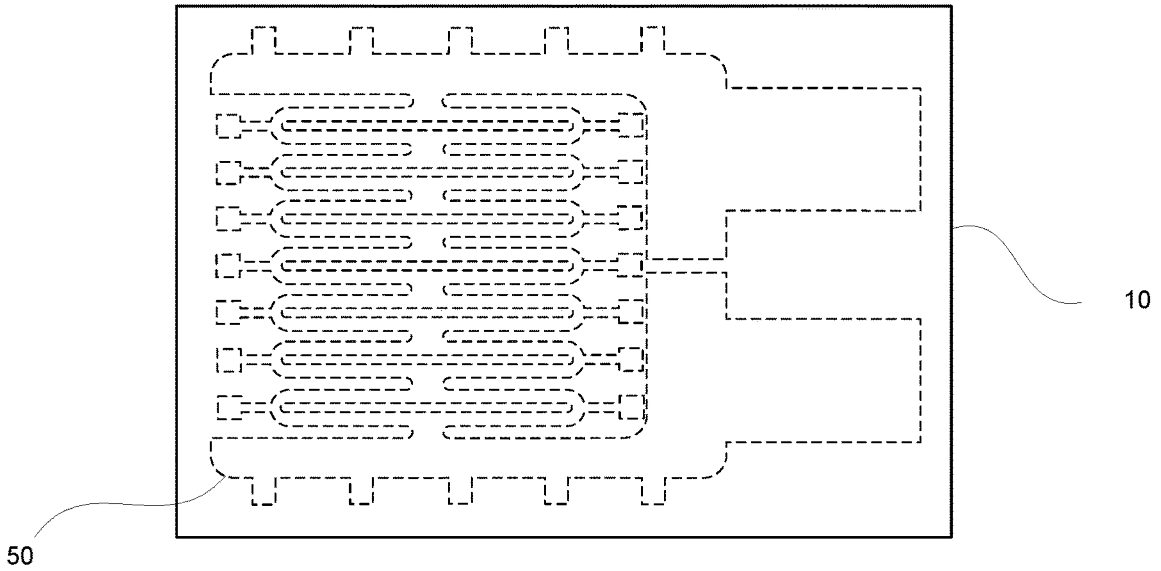
FIG. 3 is a schematic view of a heating element pattern superimposed on a surface of a sheet of conductive material according to an embodiment of the invention.

FIG. 2 illustrates a thin plate heating element 250 according to an embodiment of the invention. The heating element 250 is formed from a single planar sheet of electrically conductive material having a constant sheet thickness. The material and thickness used may be selected to provide a desired combination of electrical and thermal properties as well as a desired degree of structural integrity and/or rigidity. Illustrative materials that could be used include carbon, graphite, metals, metal alloys, electrically conductive ceramics (such as, for example, molybdenum disilicide), and composite materials made of a ceramic material and a metallic material. Composite materials may include doped ceramics such as doped silicon carbides. Suitable metals may include titanium, zirconium, tantalum and metals from the platinum group. Suitable metal alloys may include nichrome, kanthal, stainless steel, constantan, nickel-, cobalt-, chromium-, aluminum-, titanium-zirconium-, hafnium-, niobium-, molybdenum-, tantalum-, tungsten-, tin-, gallium-, manganese- and iron-containing alloys, and superalloys based on nickel, iron, cobalt, stainless steel, Timetal®, iron-aluminum based alloys and iron-manganese-aluminum based alloys. Typical sheet thicknesses for such materials may be in a range of 0.00005 in. to 0.15000 in. With reference to FIG. 3, the heating element 250 may be may be cut from a planar sheet of material 10 according to a pattern 50. This may be accomplished, for example, using any suitable cutting tool (e.g., a laser or water jet) or by punching or chemical etching.

The resulting thin plate heating element body 250 has a peripheral conduction portion made up of a positive support arm 251 and a negative support arm 252 and a central heating portion 253 positioned between the support arms 251, 252. The support arms 251, 252 have interior edges 258 facing inward toward one another and toward the central heating portion 253 and exterior lateral edges 259 facing outward. The interior edges 258 are parallel to one another and to a longitudinal axis 254. The positive support arm 251 includes a positive contact tab 271 and the negative support arm 252 includes a negative contact tab 272 extending in a longitudinal direction away from the central heating portion 253. The positive and negative contact tabs 271, 272 are configured for making electrical contact with corresponding elements of an electrical power circuit in communication with a power source.

In particular embodiments, the heating element 250 may have a plurality of peripheral support tabs 256 extending laterally outward from the exterior edges 259 of the support arms 251, 252. These tabs 256 may be sized and configured to engage surfaces or to be engaged by other structures in order to support and/or hold the heating element 250 in place within the structure of a micro-vaporizer.

Figure 4:
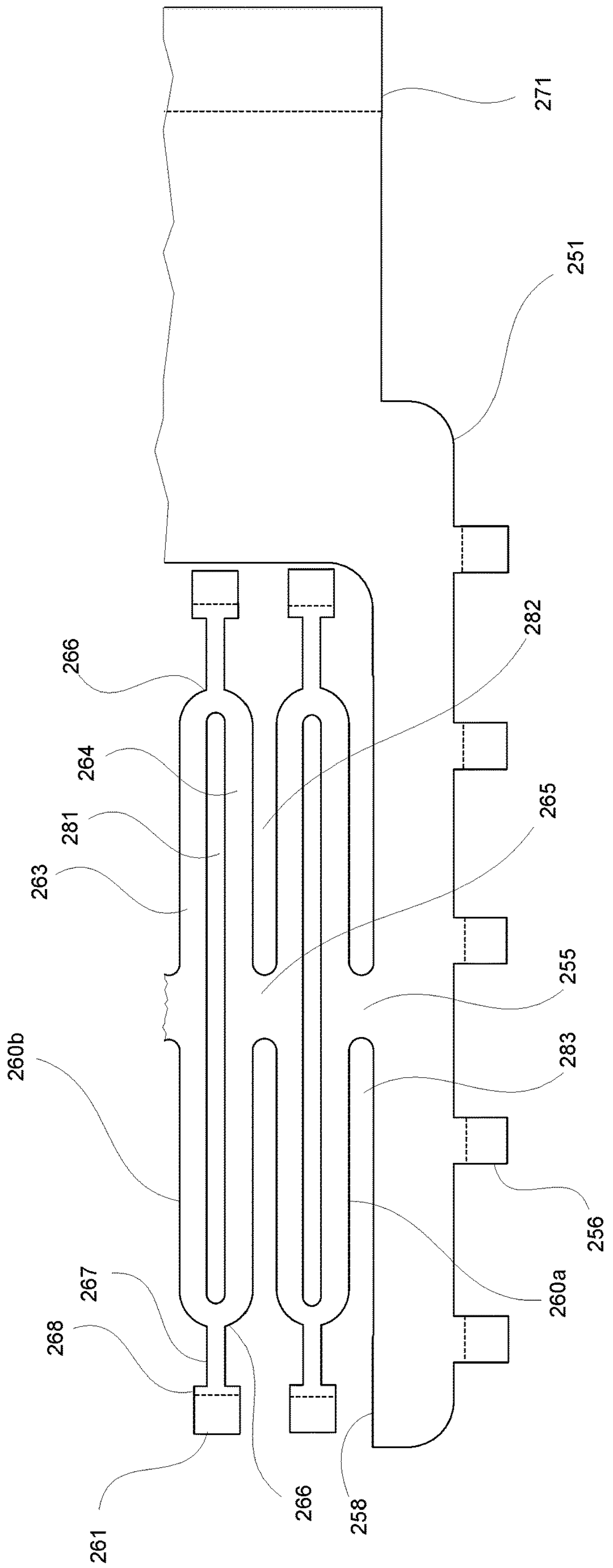
FIG. 4 is an enlarged view of a portion of the thin plate heating element of FIG. 2.

With reference to FIGS. 2 and 4, the central heating portion 253 is made up of an array of spaced apart but interconnected heating strips 269. These heating strips 269 are parallel to one another and to the longitudinal axis 254. In particular embodiments and as illustrated in FIG. 2, the heating strips 269 are divided in to pairs, with the strips 269 of each pair being connected to one another at both ends to form a heating element loop 260 surrounding a through channel 281 through the material. In the illustrated embodiment, the loop ends 266 are arcuate, but it will be understood that in other embodiments, the end connections could be straight, thereby forming a "squared off" loop. Adjacent heating element loops 260 (e.g., loop 260*a* and loop 260*b*) are connected to one another by a lateral strip 265. Adjacent strips 269 of adjacent loops 260 combine with the adjoining lateral strips 265 to define through channels 282 between the adjacent loops 260. The two heating loops 260 adjacent to the interior edges 258, 259 are connected to the adjacent interior edge 258 by a lateral bridge strip 255. The side strips 269 of these loops combine with their adjacent interior edges 258 and the lateral bridge strips 255 to define through channels 283 between the loops 260 and the supporting arm edges 258, 259.

In particular embodiments, the central heating portion 253 includes central support tabs 261 extending longitudinally from the ends of the heating strips 269. As shown in the illustrated embodiment, the central support tabs 261 may extend from the ends 266 of the heating element loops 260. Each central support tab 261 may be T-shaped with a stem 267 and a rectangular head 268. The tabs 261 may be sized and configured to engage surfaces or to be engaged by other structures in order to support and/or hold the central heating portion 253 of the heating element 250 in place within the structure of a micro-vaporizer. While the illustrated embodiment has two tabs 261 for each loop 260, it will be understood that in other embodiments, some loops 260 may have a tab 261 at just one end or may have no tabs 261 at all.

The two lateral bridge strips 255 serve to electrically connect the central heating portion 253 to the positive and negative support arms 251, 252. Aside from the bridge strips 255, the central heating portion 253 is otherwise isolated from the supporting arms 251, 252, thereby minimizing heat conduction from the central heating portion 253 to the supporting arms 251, 252. The array of heating strips 269 of the central heating portion 253 may be sized and configured to produce a heating profile for heating the spaces on both sides of the heating element 250 and vaporizable liquid within these spaces and/or passing through the channels 281, 282, 283. The array of heating strips 269 in combination with the support arms 251, 252 may also be sized to produce a particular flow area for passage of liquid and vaporization products through the heating element 250. The combination may be further configured to provide a desired overall heating element electrical resistance (i.e., the resistance between the positive and negative contact tabs 271, 272). Suitable combinations may provide an overall heating element resistance in a range of 0.0010 ohm to 5.2000 ohms. In certain embodiments, suitable combinations have been structured to provide an overall resistance in a range of 0.0015 ohm to 3.00000 ohms, and in more particular embodiments, in a range of 0.3500 ohm to 0.8000 ohm. It will be understood that the specific configuration of the central heating portion 254 and/or thickness of the heating element 250 may be tailored (in some cases, along with the power source) to the vaporizable liquid. For example, some liquids such as those containing CBD, may need to be vaporized at a lower power to prevent scorching or burning.

Figure 5:
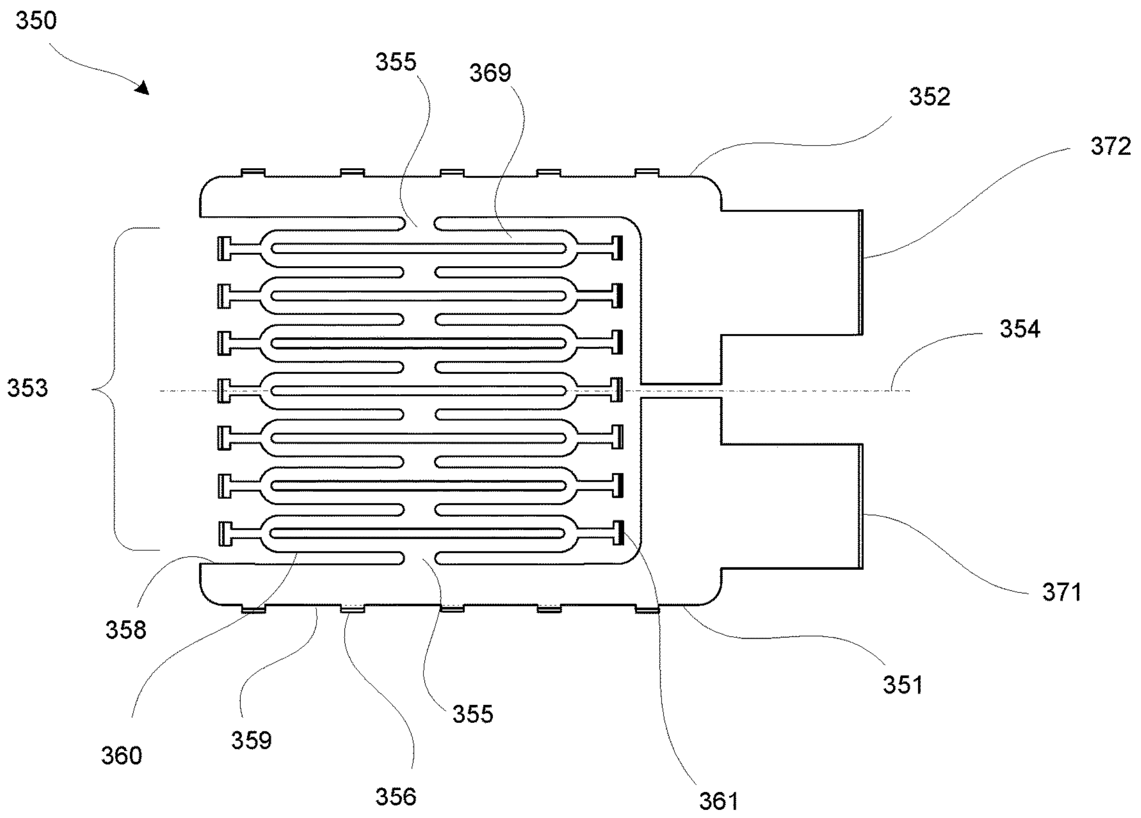
FIG. 5 is a plan view of a thin plate heating element according to an embodiment of the invention.
Figure 6:
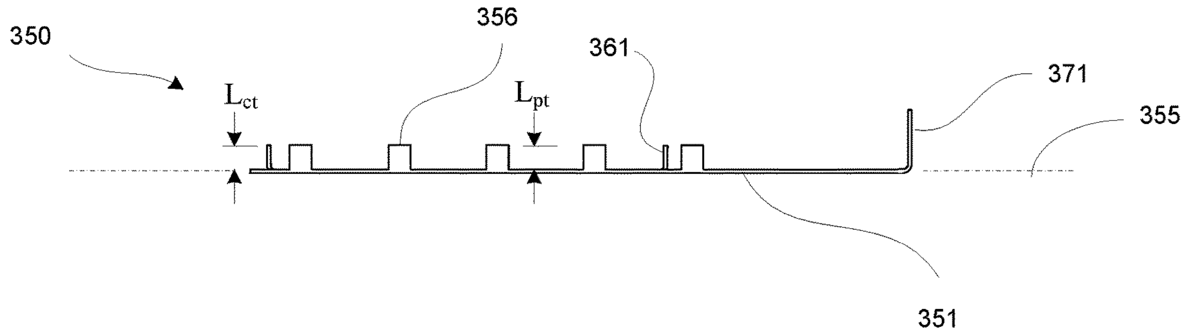
FIG. 6 is a side view of the thin plate heating element of FIG. 5.
Figure 7:
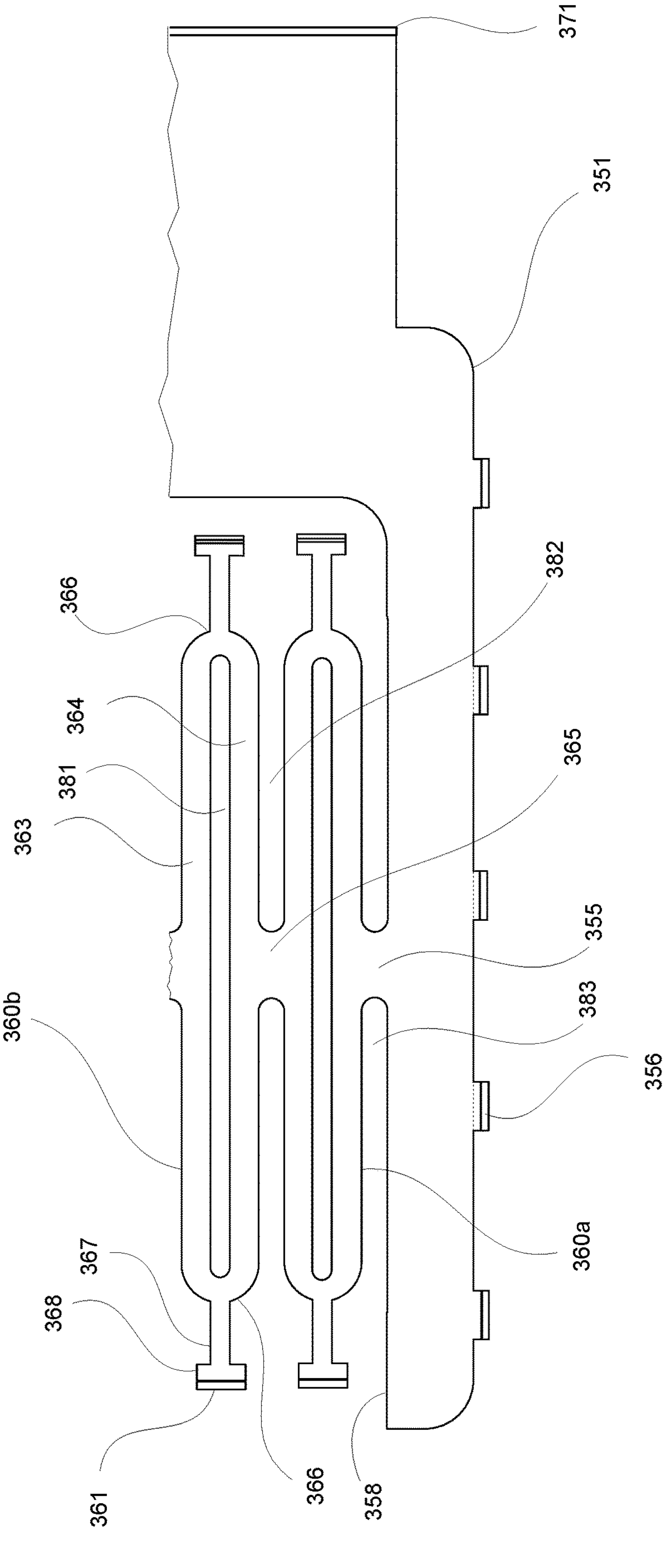
FIG. 7 is an enlarged view of a portion of the thin plate heating element of FIG. 5.
Figure 8:
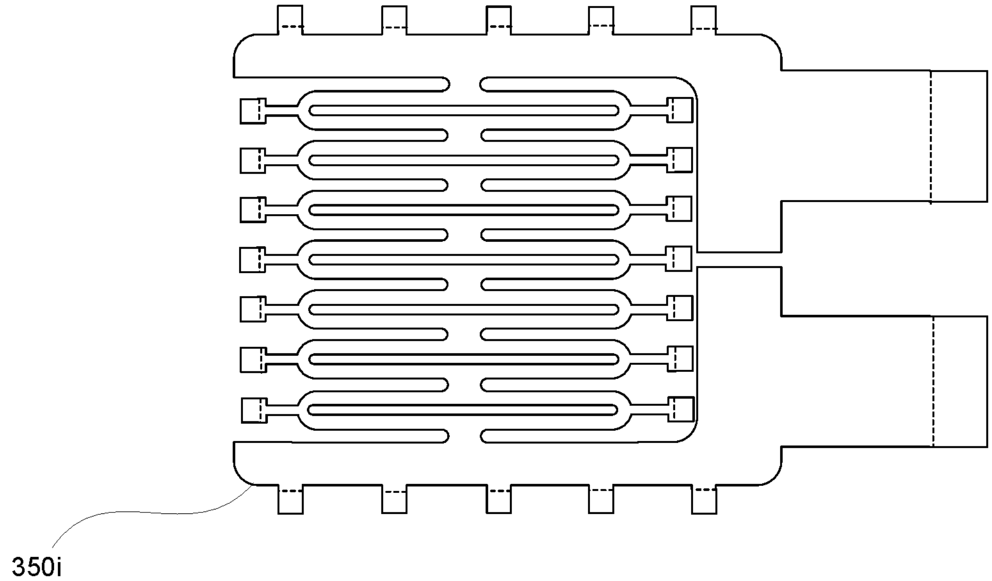
FIG. 8 is a plan view of a thin plate heating element blank according to an embodiment of the invention.

FIGS. 5-7 illustrate a thin plate heating element 350 according to another embodiment of the invention. As in the previous embodiment, the heating element 350 is formed from a single planar sheet of electrically conductive material having a constant sheet thickness. In this embodiment, however, the heating element 350 includes stand-offs extending at an angle (or angles) from its main body.

The thin plate heating element 350 has a peripheral conduction portion made up of a positive support arm 351 and a negative support arm 352 and a central heating portion 353 positioned between the support arms 351, 352. The support arms 351, 352 have interior edges 358 facing inward toward one another and toward the central heating portion 353 and exterior lateral edges 359 facing outward. The interior edges 358 are parallel to one another and to a longitudinal axis 354. The positive support arm 351 includes a positive contact tab 371 and the negative support arm 352 includes a negative contact tab 372 extending in a longitudinal direction away from the central heating portion 353. In some embodiments (e.g., the illustrated embodiment), at least a portion of the contact tabs 371, 372 angle away from the plane defined by the support arms 351, 352. In particular embodiments, the contact tabs 371, 372 include a portion at right angles to the plane of the support arms 351, 352. The positive and negative contact tabs 371, 372 are configured for making electrical contact with corresponding elements of an electrical power circuit in communication with a power source.

The heating element 350 has a plurality of peripheral support tabs 356 extending from each support arm exterior edge 359. At least a portion of each tab 356 extends upward or downward from the exterior edge at an angle relative to the surface of the support arm adjacent the exterior edge 359. In particular embodiments where the central heating portion 353 and the support arms 351, 352 are coplanar, the peripheral support tabs 356 each extend at a right angle from the plane of the central heating portion 353 and the support arms 351, 352. In some embodiments (including the illustrated embodiment), all of the peripheral support tabs 356 extend in the same direction, while in others, some tabs 356 may extend in one direction and other tabs may extend in the opposite direction. While in typical embodiments, all of the tabs 356 extending in the same direction will have the same length $L_{pt}$, in some embodiments the tabs 356 may have varying lengths to accommodate variable structures within the vaporizer.

The central heating portion 353 is made up of an array of spaced apart but interconnected heating strips 369. These heating strips 369 are parallel to one another and to the longitudinal axis 354. In particular embodiments, the heating strips 369 are divided in to pairs, with the strips 369 of each pair being connected to one another at both ends to form a heating element loop 360 surrounding a through channel 381 through the material. In the illustrated embodiment, the loop ends 366 are arcuate, but it will be understood that in other embodiments, the end connections could be straight, thereby forming a "squared off" loop. Adjacent heating element loops 360 (e.g., loop 360*a* and loop 360*b*) are connected to one another by a lateral strip 365. Adjacent strips 369 of adjacent loops 360 combine with the adjoining lateral strips 365 to define through channels 382 between the adjacent loops 360. The two heating loops 360 adjacent to the interior edges 358, 359 are connected to the adjacent interior edge 358 by a lateral bridge strip 355. The side strips 369 of these loops combine with their adjacent interior edges 358 and the lateral bridge strips 355 to define through channels 383 between the loops 360 and the supporting arm edges 358, 359.

The central heating portion 353 includes central support tabs 361 extending longitudinally from the ends of the heating element loops 360. Each central support tab 361 may have a stem 367 and a tab head 368. At least a portion of each tab head 361 extends upward or downward from the heating element loop 360 at an angle relative to the surface of the loop 360. In particular embodiments where the central heating portion 353 and the support arms 351, 352 are coplanar, the central support tabs 361 each extend at a right angle from the plane of the central heating portion 353 and the support arms 351, 352. In some embodiments (including the illustrated embodiment), all of the peripheral support tabs 361 extend in the same direction, while in others, some tabs 361 may extend in one direction and other tabs 361 may extend in the opposite direction. While in typical embodiments, all of the tabs 361 extending in the same direction will have the same extension length (i.e., the length of the portion of the tab head 368 extending away from the main plane) $L_{ct}$, in some embodiments the tab head extension portions may have varying lengths to accommodate variable structures within the vaporizer.

The peripheral support tabs 356 and the central support tabs 361 may be sized and configured to engage surfaces or to be engaged by other structures in order to support and/or hold the central heating portion 353 of the heating element 350 in place within the structure of a micro-vaporizer. In some embodiments, the peripheral support tabs 356 may all extend in one direction away from the main plane of the heating element 350 while the central support tabs 361 extend in the opposite direction away from the main plane of the heating element 350. When all of the peripheral and central support tabs 356, 361 extend in the same direction (as in the illustrated embodiment), their lengths $L_{pt}$ and $L_{ct}$ may be the same in order to provide support relative to a constant planar surface parallel to the main plane of the heating element 350.

As in the previous embodiment, the two lateral bridge strips 355 serve to electrically connect the central heating portion 353 to the positive and negative support arms 351, 352. Aside from the bridge strips 355, the central heating portion 353 is otherwise isolated from the supporting arms 351, 352. The array of heating strips 369 of the central heating portion 353 may be sized and configured as previously described.

The heating element 350 may be formed from the planar sheet of material 10 of FIG. 3. In this case, the pattern 50 may be used to cut an element blank 350*i* as a precursor to the final element 350. The blank 350*i* may be produced using any suitable cutting tool (e.g., a laser or water jet) or by punching or chemical etching. The heating element 350 may then be formed from the blank 350*i* by bending portions of the blank structure at predetermined locations (identified by dashed lines) to form the peripheral and central support tabs 356, 361 and the contact tabs 371, 372.

Figure 9:
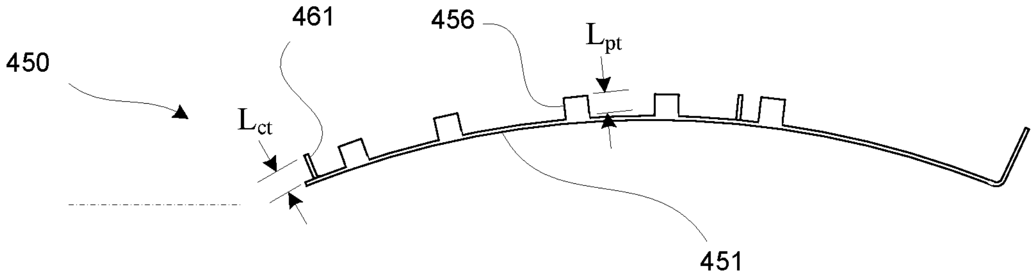
FIG. 9 is a side view of a thin plate heating element according to an embodiment of the invention.

In the previous embodiments, the positive and negative support arms and the central heating portion remain in a coplanar condition as cut from the planar material sheet. As shown in FIG. 9, however, a thin plate heating element 450 according to an embodiment of the invention may be formed from a similar planar blank into an arcuate (arched) structure. The heating element 450 may have support arms and a central heating portion (only the positive support arm 451 is visible in FIG. 9) with similar features to the previous embodiments, but is curved to match a supporting (or to-be-supported) structure of the vaporizer. The heating element 450 has peripheral support tabs 456 and central support tabs 461. Each peripheral support tab 456 extends away from the exterior support arm edge in a direction normal to the arcuate surface of the support arm. Each central support tab 461 has a portion that extends away from the central heating element in a direction normal to the arcuate surface defined by the central heating element.

The thin plate heating elements of the invention may be incorporated into a wide variety of vaporizer configurations. Of particular interest are configurations in which the heating element provides an entrance for vaporizable liquid into the vaporization chamber or vaporization portion of an air flow passage of the device. In such configurations, the heating element may form a portion of the boundary defining the vaporization chamber or vaporization section of a flow passage.

Figure 10:
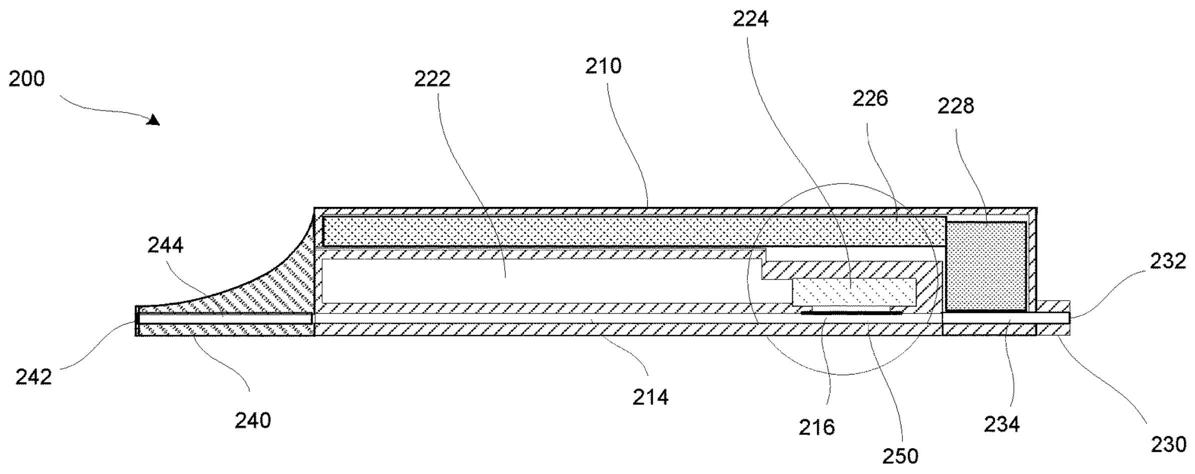
FIG. 10 is a section view of a vaporizer according to an embodiment of the invention.
Figure 11:
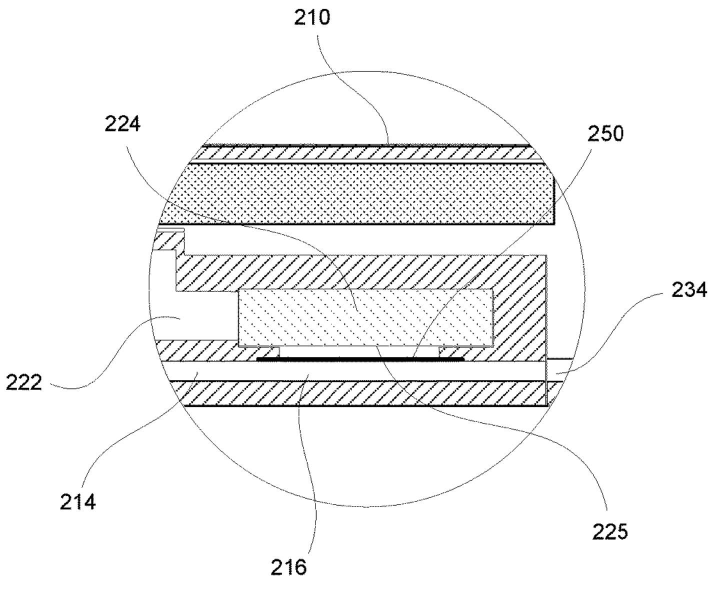
FIG. 11 is an enlarged view of a portion of the vaporizer of FIG. 10.

FIGS. 10 and 11 illustrate an exemplary micro-vaporizer 200 according to an embodiment of the invention in which the thin plate heating element 250 of FIG. 2 is incorporated. The micro-vaporizer 200 has a case or main body 210 to which is attached an air intake section 230 and a mouthpiece section 240. The main body 210 may be a single integral structure or may be made up of multiple sub-structures. The air inlet section 230 has an air intake passage 234 in communication with an air inlet 232 through which air may be drawn from the atmosphere surrounding the vaporizer 200. The mouthpiece section 240 has a vaporization products exit passage 244 in communication with an exit port 242 through which vaporization products may be drawn (e.g., by inhalation by a user). Within the main body 210 of micro-vaporizer 200 is disposed a main passageway 214 in communication with the intake passage 234 and the exit passage 244. A portion of the main passageway 214 may be configured to provide a vaporization section 216 that is partially defined by the thin plate heating element 250.

Also disposed within the main body 210 is a reservoir 222 configured for receiving a vaporizable liquid and a fluid transport structure 224. The liquid reservoir 222 may be configured as a simple tank in which the liquid is disposed. In some embodiments, the reservoir 222 may comprise an adsorptive or absorptive material or structure that retains the vaporizable liquid. The fluid transport structure 224 is configured for drawing vaporizable liquid from the reservoir 222 and transporting it to a surface adjacent or in contact with the heating element 250. Typically, the fluid transport structure 224 may be or comprise a wick or other structure configured for using capillary action to move the liquid from the reservoir 222 toward the heating element 250. In particular embodiments, the fluid transport structure may be or comprise a composite wick structure similar to those described in U.S. application Ser. No. 25/639,139 (the "'139 Patent"), the complete disclosure of which is incorporated herein by reference. In some embodiments, the fluid transport structure may be or include a pumping arrangement. The vaporizer 200 also includes a power source (e.g., a battery) 226 in electrical communication with a control processor 228 and the heating element 250. The vaporizer 200 may also include an activation mechanism (not shown) that allows a user to selectively activate the device, thereby causing power to flow from the power source 226 to the heating element 250. Upon activation, vaporizable liquid, typically comprising one or more active materials, is drawn from the reservoir 222 and brought into close proximity to the heating element 250, thereby heating the liquid. Vapor products and/or unvaporized liquid are drawn through the heating element 250 into the vaporization section 216 where they are further heated. In the vaporization section 216, vaporized liquid is mixed with air drawn into and through the air inlet passage 234. The resulting mixture of air and vaporization products is then drawn through the passageway 214 into and through the mouthpiece passage 244 and out through the exit port 242.

It will be understood that there may be many other configurations of the passageways upstream and downstream of the vaporization chamber. In some configurations, there may be multiple air inlet ports and the air flow path from the air inlet ports to the vaporization chamber may comprise one or more intermediate passageways and/or chambers.

As used herein, the term "active material" refers to any material that controllably alters or adds to the vaporization products of the device. Depending on the application, active materials can include, without limitation, plant material, minerals, deodorizing agents, fragrances, insect repellants, medications, and disinfectants and any material or structure containing or incorporating any of the foregoing.

In the specific instance of personal vaporizers, active materials may include flavorant substances that augment the flavorant of the vaporizable liquid. These may include, without limitation, marijuana, hemp, cannabidiol (cbd), citronella, geraniol, mint, thyme, tobacco, *Salvia dorrii, salvia, Passiflora incarnata, Arctostaphylos uva-ursi, Lobelia inflata*, lemon grass, cedar wood, clove, cinnamon, coumarin, helio, vanilla, menthol, *eucalyptus*, peppermint, rosemary, lavender, licorice, and cocoa and any material or structure containing or incorporating any of the foregoing.

As best seen in FIG. 11, the planar thin plate heating element 250 is positioned so that it is parallel to the direction of air flow into and through the vaporization section 216 and so that it, in effect, provides a part of the boundary surrounding the vaporization section 216. In some embodiments, the peripheral support elements 256 may be used to attach the heating element 250 to the internal structure of the vaporizer, thereby minimizing conductive heat transfer from the heating element 250 to the structure. When the heating element 250 is activated, the upper surface of the heating element 250 heats the lower surface 225 of the liquid transport element 224 and the vaporizable liquid therein. This causes the liquid to vaporize and to draw more liquid from the reservoir 222 through the liquid transport structure 224. Inhalation by the user draws vapor products and/or liquid through the passages 281, 282, 283 in the heating element 250 and into the vaporization section 216.

The heating element 250 may be configured to minimize heat conduction from the central heating portion 253. This may allow the heating element to be mounted directly to molded plastic structural elements of the vaporizer 200 without the need for gasketing, thermal insulation or other intermediate material.

Figure 12:
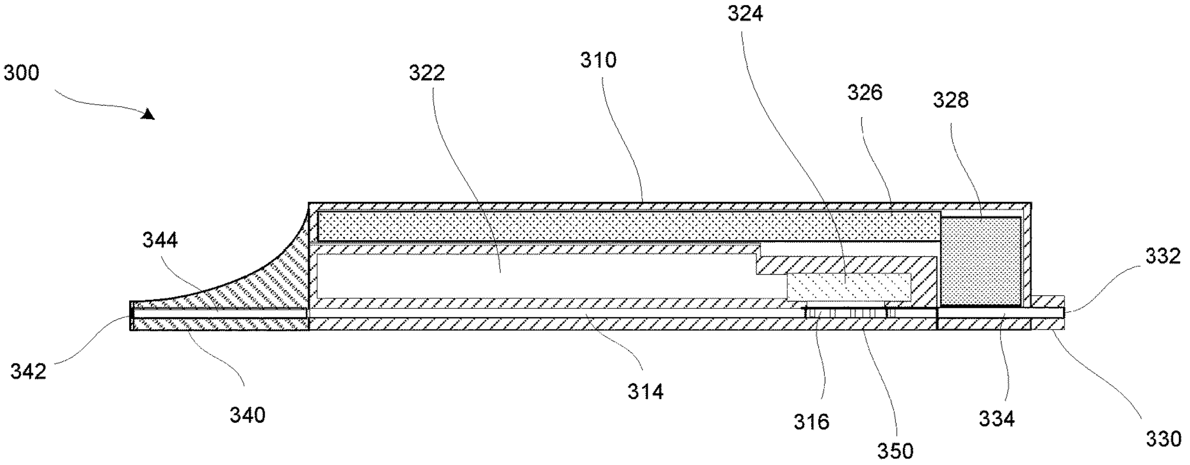
FIG. 12 is a section view of a vaporizer according to an embodiment of the invention.
Figure 13:
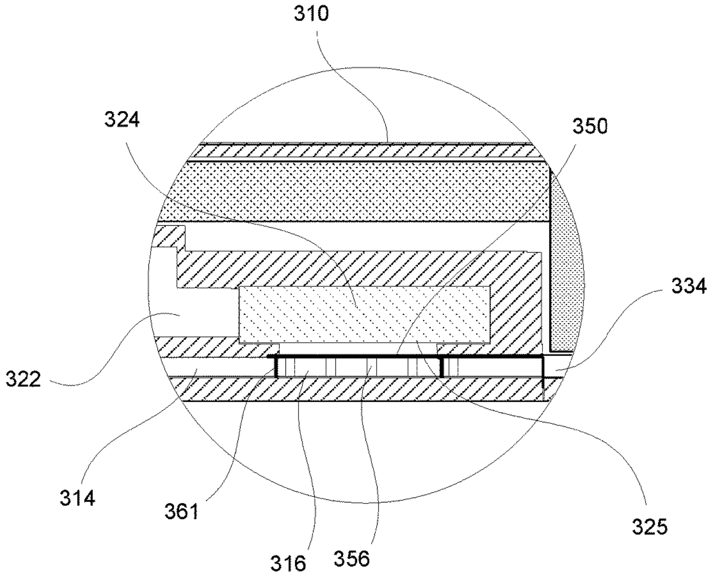
FIG. 13 is an enlarged view of a portion of the vaporizer of FIG. 12.

FIGS. 12 and 13 illustrate an exemplary micro-vaporizer 300 according to an embodiment of the invention in which the thin plate heating element 350 of FIG. 5 is incorporated. The micro-vaporizer 300 has a case or main body 310 to which is attached an air intake section 330 and a mouthpiece section 340. The main body 310 may be a single integral structure or may be made up of multiple sub-structures. The air inlet section 330 has an air intake passage 334 in communication with an air inlet 332 through which air may be drawn from the atmosphere surrounding the vaporizer 300. The mouthpiece section 340 has a vaporization products exit passage 344 in communication with an exit port 342 through which vaporization products may be drawn. Within the main body 310 of micro-vaporizer 300 is disposed a main passageway 314 in communication with the intake passage 334 and the exit passage 344. A portion of the main passageway 314 may be configured to provide a vaporization section 316 that is partially defined by the thin plate heating element 350.

Also disposed within the main body 310 is a reservoir 322 configured for receiving a vaporizable liquid and a fluid transport structure 324. Typically, the fluid transport structure 324 may be or comprise a wick or other structure configured for using capillary action to move the liquid from the reservoir 322 toward the heating element 350. In particular embodiments, the fluid transport structure may be or comprise a composite wick structure similar to those described in the '139 patent. The vaporizer 300 also includes a power source (e.g., a battery) 326 in electrical communication with a control processor 328 and the heating element 350. The vaporizer 300 may also include an activation mechanism (not shown) that allows a user to selectively activate the device, thereby causing power to flow from the power source 326 to the heating element 350. Upon activation, vaporizable liquid, typically comprising one or more active materials, is drawn from the reservoir 322 and brought into close proximity to the heating element 350, thereby heating the liquid. Vapor products and/or unvaporized liquid are drawn through the heating element 350 into the vaporization section 316 where they are further heated. In the vaporization section 316, vaporized liquid is mixed with air drawn into and through the air inlet passage 334. The resulting mixture of air and vaporization products is then drawn through the passageway 314 into and through the mouthpiece passage 344 and out through the exit port 342.

As best seen in FIG. 13, the thin plate heating element 350 is positioned so that the planar main body of the heating element (i.e., the support arms 371, 372 and the central heating portion 353) is parallel to the direction of air flow into and through the vaporization section 316 and so that it, in effect, provides a part of the boundary surrounding the vaporization section 316. In this embodiment, the peripheral support tabs 356 and the central support tabs 361 are sized to contact the floor of the vaporization section 316. This serves to support and maintain the spacing of the support arms 371, 372 and the central heating portion 353 from the floor of the vaporization section 316.

As before, when the heating element 350 is energized, the upper surface of the heating element 350 heats the lower surface 325 of the liquid transport element 324 and the vaporizable liquid therein. This causes the liquid to vaporize and to draw more liquid from the reservoir 322 through the liquid transport structure 324. Inhalation by the user draws vapor products and/or liquid through the passages 381, 382, 383 in the heating element 350 and into the vaporization section 316.

The heating element 350 may be configured to minimize heat conduction from the central heating portion 253 to the peripheral support tabs 356 and/or central support tabs 361. This may allow the heating element 350 to be mounted directly to molded plastic structural elements of the vaporizer 300 without the need for gasketing, thermal insulation or other intermediate material.

Figure 14:
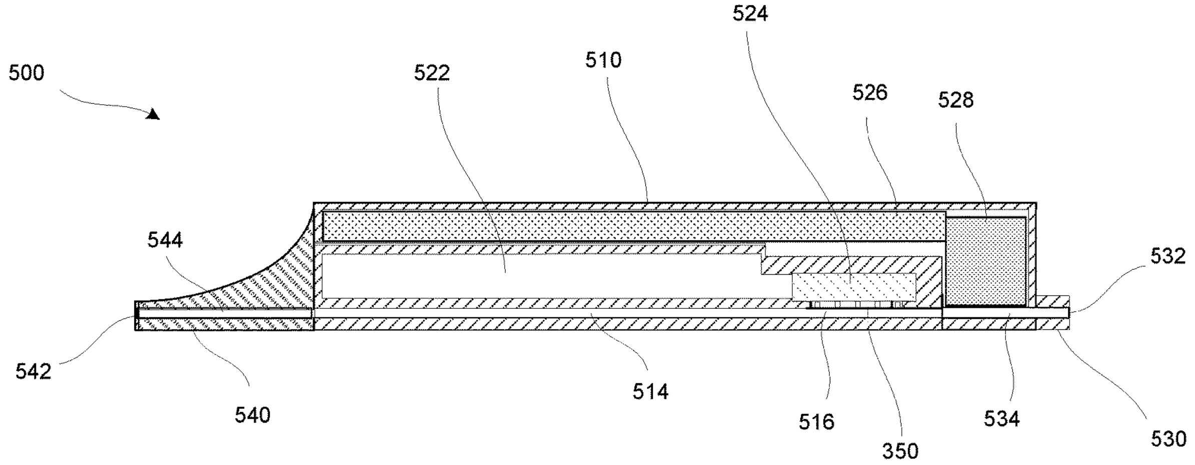
FIG. 14 is a section view of a vaporizer according to an embodiment of the invention.
Figure 15:
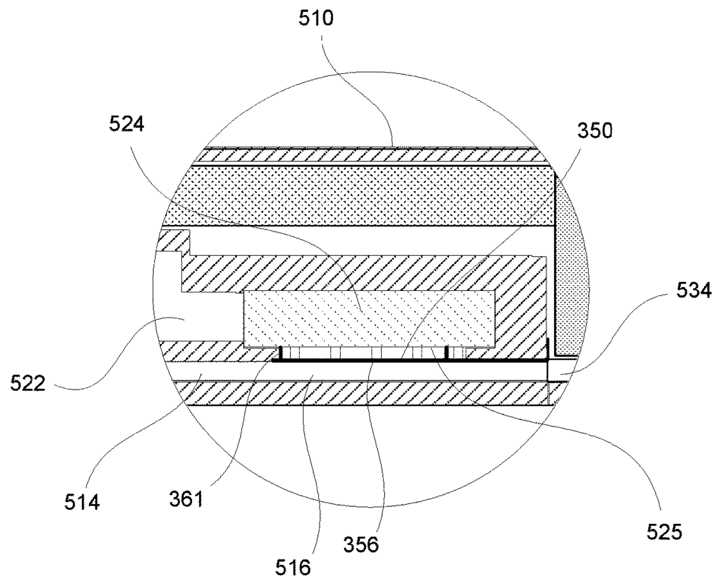
FIG. 15 is an enlarged view of a portion of the vaporizer of FIG. 14.

FIGS. 14 and 15 illustrate an exemplary micro-vaporizer 500 according to another embodiment of the invention in which the thin plate heating element 350 of FIG. 5 is incorporated. The micro-vaporizer 500 has a case or main body 510 to which is attached an air intake section 530 and a mouthpiece section 540. The main body 510 may be a single integral structure or may be made up of multiple sub-structures. The air inlet section 530 has an air intake passage 534 in communication with an air inlet 532 through which air may be drawn from the atmosphere surrounding the vaporizer 500. The mouthpiece section 540 has a vaporization products exit passage 544 in communication with an exit port 542 through which vaporization products may be drawn. Within the main body 510 of micro-vaporizer 500 is disposed a main passageway 514 in communication with the intake passage 534 and the exit passage 544. A portion of the main passageway 514 may be configured to provide a vaporization section 516 that is partially defined by the thin plate heating element 350.

Also disposed within the main body 510 is a reservoir 522 configured for receiving a vaporizable liquid and a fluid transport structure 524. Typically, the fluid transport structure 524 may be or comprise a wick or other structure configured for using capillary action to move the liquid from the reservoir 522 toward the heating element 350. In particular embodiments, the fluid transport structure may be or comprise a composite wick structure similar to those described in the '139 patent. The vaporizer 500 also includes a power source (e.g., a battery) 526 in electrical communication with a control processor 528 and the heating element 350. The vaporizer 500 may also include an activation mechanism (not shown) that allows a user to selectively activate the device, thereby causing power to flow from the power source 526 to the heating element 350. Upon activation, vaporizable liquid, typically comprising one or more active materials, is drawn from the reservoir 522 and brought into close proximity to the heating element 350, thereby heating the liquid. Vapor products and/or unvaporized liquid are drawn through the heating element 350 into the vaporization section 516 where they are further heated. In the vaporization section 516, vaporized liquid is mixed with air drawn into and through the air inlet passage 534. The resulting mixture of air and vaporization products is then drawn through the passageway 514 into and through the mouthpiece passage 544 and out through the exit port 542.

As best seen in FIG. 15, the orientation of the thin plate heating element 350 is reversed from that of the previous embodiment. The heating element 350 is again positioned so that the planar main body (i.e., the support arms 371, 372 and the central heating portion 353) is parallel to the direction of air flow into and through the vaporization section 516. In this embodiment, however, support tabs 356, 361 extend upward and are sized to contact the lower surface 525 of the liquid transport element 524. This serves to maintain the spacing of the support arms 371, 372 and the central heating portion 353 from the lower surface 525 of the liquid transport element 524.

As before, when the heating element 350 is energized, the upper surface of the heating element 350 heats the lower surface 525 of the liquid transport element 524 and the vaporizable liquid therein. This causes the liquid to vaporize and to draw more liquid from the reservoir 522 through the liquid transport structure 524. Inhalation by the user draws vapor products and/or liquid through the passages 381, 382, 383 in the heating element 350 and into the vaporization section 516.

While the foregoing illustrates and describes exemplary embodiments of this invention, it is to be understood that the invention is not limited to the construction disclosed herein. The invention can be embodied in other specific forms without departing from the spirit or essential attributes.

What is claimed is:

1. A vaporizer heating element comprising:

a heating element body formed from a single planar sheet of electrically conductive material having a constant sheet thickness, the heating element body comprising:

a peripheral conduction portion comprising spaced apart positive and negative support arms, the positive support arm having an interior edge and an exterior edge opposite the interior edge of the positive support arm, the negative support arm having an interior edge and an exterior edge opposite the interior edge of the negative support arm, at least a portion of the interior edge of the positive support arm being parallel to at least a portion of the interior edge of the negative support arm;

a central heating portion comprising a plurality of spaced apart parallel heating strips that are thinner than the positive and negative support arms, spaces between said heating strips defining first flow channels through the heating element body, the central heating portion being intermediate, but spaced apart from the interior edge of the positive support arm and the interior edge of the negative support arm so that there is a gap between the wider positive support arm and a first one of the thinner heating strips and there is a gap between the wider negative support arm and a second one of the thinner heating strips;

a first bridge strip connecting the positive support arm to the central heating portion;

a second bridge strip connecting the negative support arm to the central heating portion;

a first plurality of peripheral support tabs extending from the exterior edge of the positive support arm in a first direction;

a second plurality of peripheral support tabs extending from the exterior edge of the negative support arm in a second direction opposite the first direction; and a plurality of central support tabs extending from the central heating portion, wherein the positive support arm and the negative support arm are on opposite sides of a longitudinal body axis that bisects the vaporizer heating element, wherein a portion of the exterior surface of the positive support arm from which the first plurality of peripheral support tabs extend is the portion of the exterior surface of the positive support arm that is furthest from the longitudinal body axis, and wherein a portion of the exterior surface of the negative support arm from which the second plurality of peripheral support tabs extend is the portion of the exterior surface of the negative support arm that is furthest from the longitudinal body axis.

2. A vaporizer heating element according to claim 1, wherein the peripheral conduction portion, the central heating portion, and the first and second bridge strips are coplanar and define an element body plane.

3. A vaporizer heating element according to claim 2, wherein at least a portion of each peripheral support tab and at least a portion of each central support tab is perpendicular to the element body plane.

4. A vaporizer heating element according to claim 3, wherein the at least a portion of each peripheral support tab has a peripheral stand-off length and the at least a portion of each central support tab has a central stand-off length.

5. A vaporizer heating element according to claim 4, wherein the peripheral stand-off length is the same as the central stand-off length.

6. A vaporizer heating element according to claim 1, wherein the central heating portion comprises:

an array of spaced apart closed loops, each loop having a pair of parallel side strips connected to one another at first and second loop ends, the parallel side strips of the closed loops all being parallel to one another and to the interior edges of the positive and negative support arms, wherein each pair of adjacent loops are connected to one another by a lateral strip.

7. A vaporizer heating element according to claim 6, wherein each of the central support tabs extends from one of the loop ends.

8. A vaporizer heating element according to claim 1, further comprising:

a positive contact tab extending from an end of the positive support arm; and a negative contact tab extending from an end of the negative support arm.

9. A vaporizer heating element according to claim 8, wherein at least a portion of each contact tab is at an angle relative to the support arm from which the contact tab extends.

10. A vaporizer heating element according to claim 8, wherein an electrical resistance between the positive and negative contact tabs is in a range of 0.0010 ohm to 5.2000 ohms.

11. A vaporizer heating element according to claim 8, wherein an electrical resistance between the positive and negative contact tabs is in a range of 0.0015 ohm to 3.0000 ohms.

12. A vaporizer heating element according to claim 1, wherein the sheet thickness is in a range of 0.00005 in. to 0.15000 in.

13. A vaporizer heating element according to claim 1, wherein the electrically conductive material is one of the set consisting of a carbon material or carbon composite, an electrically conductive ceramic, and a metal or metal alloy.

14. A vaporizer heating element according to claim 1, wherein the electrically conductive material is one of the set consisting of nichrome, ferritic iron-chromium-aluminum alloy, stainless steel, copper-nickel alloy, nickel-, cobalt-, chromium-, aluminum-, titanium-, zirconium-, hafnium-, niobium-, molybdenum-, tantalum-, tungsten-, tin-, gallium-, manganese- and other iron-containing alloys.

15. A vaporizer heating element according to claim 1, wherein the peripheral conduction portion, central heating portion, and first and second bridge strips collectively form an arcuate body member defining a constant arcuate cross-sectional shape.

16. A vaporizer heating element according to claim 1, wherein each peripheral support tab and each central support tab has a cantilever structure.

17. A vaporizer heating element according to claim 1, wherein the plurality of central support tabs extend from the central heating portion in a direction that is perpendicular to the first and second directions.

18. A vaporizer heating element according to claim 1, wherein the plurality of central support tabs comprises:

a first set of central support tabs that extend from the central heating portion in a third direction that is perpendicular to the first and second directions, and a second set of central support tabs that extend from the central heating portion in a fourth direction that is perpendicular to the first and second directions and is opposite the third direction.

19. A vaporizer heating element according to claim 18, wherein the positive and negative support arms extend around the central heating portion to form a containing space that contains the central heating portion, the containing space being open on one side, and wherein the first set of central support tabs extend from the central heating portion toward the open side of the containing space and the second set of central support tabs extend from the central heating portion toward a closed side of the containing space.

20. A vaporizer heating element according to claim 1, wherein the first plurality of peripheral support tabs extend further in the first direction than the positive support arm, and wherein the second plurality of peripheral support tabs extend further in the second direction than the negative support arm.

21. A vaporizer heating element according to claim 1, wherein the positive support arm is continuous and uninterrupted from the entirety of the exterior edge of the positive support arm to the entirety of the interior edge of the positive support arm.

22. A vaporizer heating element comprising:

an electrically conductive element body comprising:

a planar peripheral conduction portion comprising spaced apart positive and negative support arms, each support arm having an interior edge and an exterior edge, at least portions of the interior and exterior edges being parallel to a longitudinal body axis that bisects the vaporizer heating element so that the positive and negative support arms are on opposite sides of the longitudinal body axis;

a first plurality of peripheral support tabs extending from a portion of the exterior edge of the positive support arm in a first direction away from the longitudinal body axis, the portion of the exterior edge of the positive support arm being the furthest portion of the exterior surface of the positive support arm from the longitudinal body axis;

a second plurality of peripheral support tabs extending from a portion of the exterior edge of the negative support arm in a second direction that is opposite the first direction and away from the longitudinal body axis, the portion of the exterior edge of the negative support arm being the furthest portion of the exterior surface of the negative support arm from the longitudinal body axis; and a planar central heating portion comprising:

an array of spaced apart closed loops, each loop having a pair of parallel edge strips connected to one another at first and second loop ends, the parallel edge strips of the closed loops all being parallel to the longitudinal body axis, and each pair of adjacent loops being connected to one another by a lateral strip;

a plurality of central support tabs, each said tab extending from one of the first and second loop ends of one of the closed loops;

a first element connector connecting the interior edge of the positive support arm to the central heating portion; and a second element connector connecting the interior edge of the negative support arm to the central heating portion, wherein the edge strips are thinner than the positive and negative support arms, and wherein there is a gap between the wider positive support arm and a first one of the thinner edge strips and there is a gap between the wider negative support arm and a second one of the thinner edge strips.

23. A vaporizer heating element according to claim 22, wherein the peripheral conduction portion, the central heating portion, and the first and second element connectors are coplanar and define an element body plane.

24. A vaporizer heating element according to claim 22, wherein the electrically conductive element body is formed from a single sheet of electrically conductive material.

25. A vaporizer heating element according to claim 22, further comprising: positive and negative contact tabs extending from an end of the positive and negative support arms respectively.

26. A vaporizer hearing element according to claim 22, wherein the plurality of central support tabs comprises:

a first set of central support tabs that extend from the central heating portion in a third direction that is parallel to the longitudinal body axis, and a second set of central support tabs that extend from the central heating portion in a fourth direction that is parallel to the longitudinal body axis and is opposite the third direction.

27. A vaporizer heating element according to claim 26, wherein the positive and negative support arms extend around the central heating portion to form a containing space that contains the central heating portion, the containing space being open on one side, the open side of the containing space being bisected by the longitudinal body axis, and wherein the first set of central support tabs extend from the central heating portion toward the open side of the containing space and the second set of central support tabs extend from the central heating portion toward a closed side of the containing space.

28. A vaporizer heating element according to claim 22, wherein the first plurality of peripheral support tabs extend further in the first direction than the positive support arm, and wherein the second plurality of peripheral support tabs extend further in the second direction than the negative support arm.

29. A vaporizer heating element according to claim 22, wherein the negative support arm is continuous and uninterrupted from the entirety of the exterior edge of the negative support arm to the entirety of the interior edge of the negative support arm.

30. A vaporizer comprising:

a housing;

a vaporization chamber disposed within the housing, the vaporization chamber being in fluid communication with an air inlet and a vaporization product outlet;

a reservoir disposed within the housing, the reservoir being configured for selectively retaining a vaporizable liquid;

a liquid transport structure having an intake surface configured for contacting vaporizable liquid in the reservoir and drawing it from the reservoir to an exit surface of the liquid transport structure; and the heating element of claim 1, wherein the heating element is positioned to form a portion of a first wall of the vaporization chamber, wherein the heating element has a first side adjacent or in contact with the exit surface of the liquid transport structure and an opposite second side facing an interior space of the vaporization chamber, wherein the central heating portion is in electrical communication with the positive and negative support arms, and wherein the peripheral support tabs each have a free end in contact with one of the set consisting of a surface of a second wall of the vaporization chamber and the exit surface of the liquid transport structure.

31. A vaporizer according to claim 30, wherein each central support tab has a free end in contact with one of the set consisting of a surface of a second wall of the vaporization chamber and the exit surface of the liquid transport structure.

32. A vaporizer according to claim 31, wherein the peripheral support tabs and the central support tabs are all in contact with the second wall of the vaporization chamber.

33. A vaporizer according to claim 31, wherein the peripheral support tabs and the central support tabs are all in contact with the exit surface of the liquid transport structure.

34. A vaporizer comprising:

a housing;

a vaporization chamber disposed within the housing, the vaporization chamber being in fluid communication with an air inlet and a vaporization product outlet;

a reservoir disposed within the housing, the reservoir being configured for selectively retaining a vaporizable liquid;

a liquid transport structure having an intake surface configured for contacting vaporizable liquid in the reservoir and drawing it from the reservoir to an exit surface of the liquid transport structure; and the heating element of claim 22, wherein the heating element is positioned to form a portion of a first wall of the vaporization chamber, wherein the heating element has a first side adjacent or in contact with the exit surface of the liquid transport structure and an opposite second side facing an interior space of the vaporization chamber, wherein the planar central heating portion is in electrical communication with the positive and negative support arms, wherein the peripheral support tabs each have a free end in contact with one of the set consisting of a surface of a second wall of the vaporization chamber and the exit surface of the liquid transport structure.

35. A vaporizer according to claim 34, wherein each central support tab has a free end in contact with one of the set consisting of a surface of a second wall of the vaporization chamber and the exit surface of the liquid transport structure.

36. A vaporizer according to claim 35, wherein the peripheral support tabs and the central support tabs are all in contact with the second wall of the vaporization chamber.

37. A vaporizer according to claim 35, wherein the peripheral support tabs and the central support tabs are all in contact with the exit surface of the liquid transport structure.

* * * * *